United States Patent [19]

Ferland et al.

[11] 4,131,745

[45] Dec. 26, 1978

[54] ARYLOXY AMINOBUTANOLS, THEIR PREPARATION AND USE THEREOF

[75] Inventors: Jean-Marie Ferland, St. Laurent; Real Laliberte, Chomeday; Wilbur Lippman, Montreal; Thomas A. Pugsley, Kirkland, all of Canada

[73] Assignee: Ayerst, McKenna & Harrison, Ltd., Montreal, Canada

[21] Appl. No.: 852,656

[22] Filed: Nov. 18, 1977

Related U.S. Application Data

[62] Division of Ser. No. 687,852, May 19, 1976, Pat. No. 4,071,552.

[51] Int. Cl.² .......................................... C07C 103/38
[52] U.S. Cl. ............................... 560/252; 260/562 A; 260/562 P
[58] Field of Search ................... 560/252; 260/562 A, 260/562 P

[56] References Cited

U.S. PATENT DOCUMENTS

| 3,337,628 | 8/1967 | Crowther et al. | 260/562 A |
| 3,432,545 | 3/1969 | Howe | 560/252 |
| 3,520,919 | 7/1970 | Crowther et al. | 560/252 |
| 4,041,075 | 8/1977 | Smith | 260/562 A |

*Primary Examiner*—Vivian Garner
*Attorney, Agent, or Firm*—Adley F. Mandel

[57] ABSTRACT

Disclosed herein are compounds of the formula

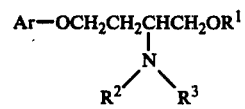

in which Ar is phenyl or 1-naphthyl; $R^1$ is hydrogen or lower alkyl; and $R^2$ and $R^3$ are either the same or different selected from the group consisting of hydrogen or lower alkyl; with the proviso that when $R^1$ is lower alkyl then $R^2$ is the same lower alkyl. The compounds are antidepressant agents and methods for their preparation and use also are disclosed.

8 Claims, No Drawings

ARYLOXY AMINOBUTANOLS, THEIR PREPARATION AND USE THEREOF

This is a division, of application Ser. No. 687,852, filed May 19, 1976, now U.S. Pat. No. 4,071,552.

BACKGROUND OF THE INVENTION a) Field of the Invention

This invention relates to aryloxy aminobutanols having antidepressant activity, to a process for their preparation, to intermediates used for the process, and to pharmaceutical compositions and a method of use for these aryloxy aminobutanols.

b) Prior Art

During the last few decades, psychotherapy has become more effective due to the adjunct use of new central nervous system agents, in particular, the use of tranquilizers and antidepressants. As a consequence the development of new and useful agents for psychotherapy has been diligently pursued, and the finding of a potent, well tolerated agent is noteworthy indeed.

The present invention discloses a group of antidepressent agents having these attributes. The agents are aryloxy aminobutanols. A number of aryloxy aminoalcohols are known to possess pharmacologic properties; for example, 1-isopropylamino-3-(1-naphthyloxy)-2-propanol, J. W. Black, et al., Lancet, 1, 1080(1964), a potent $\beta$-blocking agent, and a group of alkyl ethers of 3-amino-1-phenoxy-2-propanol derivatives, V. Dauksas and L. Pikunaite, Zh. Vses. Khim. Obshchestva im. D. I. Mendeleeva, 9, 352 (1964); Chem Abstr., 61, 6942c(1964) having a stimulating effect on the central nervous system. The compounds of the present invention are distinguished readily from the prior art compounds by having a greater number of carbon atoms and a different structural relationship with respect to the substituents.

SUMMARY OF THE INVENTION

The compounds of this invention are represented by formula 1

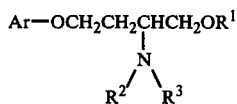

$$Ar-OCH_2CH_2CHCH_2OR^1 \quad (1)$$
$$\underset{R^2 \diagup \diagdown R^3}{N}$$

in which Ar is phenyl or 1-naphthyl; $R^1$ is hydrogen or lower alkyl; and $R^2$ and $R^3$ are either the same or different selected from the group consisting of hydrogen or lower alkyl; with the proviso that when $R^1$ is lower alkyl then $R^2$ is the same lower alkyl; or a therapeutically acceptable acid addition salt thereof.

Pharmaceutical compositions comprising the compound of formula 1, or a therapeutically acceptable acid addition salt thereof, and a pharmaceutically acceptable carrier are included within the scope of this invention.

Also included is a method for alleviating symptoms of depression in mammals by administering to said mammals an antidepressant effective amount of the compound of formula 1, or a therapeutically acceptable salt thereof.

Still another aspect of this invention includes intermediates for the preparation of the compounds of formula 1.

Details of the Invention

The term "lower alkyl" as used herein contemplates straight chain alkyl radicals containing from one to six carbon atoms and branched chain alkyl radicals containing three to four carbon atoms and includes methyl, ethyl propyl, isopropyl, butyl, isobutyl, hexyl and the like.

The term "lower alkanoyloxy" as used herein contemplates both straight and branched chain alkanoyloxy radicals containing from two to six carbon atoms and includes acetoxy, propionyloxy, hexanoyloxy and the like.

The compounds of formula 1 are capable of forming acid addition salts with therapeutically acceptable acids. Such acid addition salts are included within the scope of this invention.

The acid addition salts are prepared by reacting the corresponding base form of the compound of formula 1 with at least one equivalent, or preferably with an excess of the appropriate acid in an organic solvent, for example, ether or an ethanol-ether mixture. These salts, when administered to mammals, possess the same pharmacologic activities as the corresponding bases. For many purposes it is preferable to administer the salts rather than the base compounds. Among the acid addition salts suitable for this purpose are salts such as the sulfate, phosphate, lactate, tartrate, maleate, citrate, hydrobromide and hydrochloride. Both the base compounds and the salts have the distinct advantage of possessing a relatively low order of toxicity.

Also included in this invention are the stereochemical isomers of the compounds of formula 1 which result from asymmetric centers contained therein.

Individual optical isomers, which might be separated by fractional crystallization of the diastereoisomeric salts thereof, for instance, salts with d- or l-tartaric acid or D-(+)-$\alpha$-bromocamphor sulfonic acid, are also included.

The antidepressant activity of the compounds of formula 1 and their acid addition salts with pharmaceutically acceptable acids is demonstrated in standard pharmacologic tests such as, for example, the tests described by F. Hafliger and V. Burckhart in "Psychopharmacological Agents", M. Gordon, Ed., Academic Press, New York and London, 1964, pp. 75–83.

More specifically, as noted in the latter reference the antidepressant properties of a compound may be demonstrated by its capacity to antagonize the depressant effects of reserpine. Furthermore, it is well documented that reserpine in animals produces a model depression which can be used for detecting antidepressant properties. Accordingly, the compounds of the present invention antagonize reserpine effects in mice at doses ranging from about 1 to 100 mg/kg.

The antidepressant activity of the compounds of formula 1 is also demonstrated by the method of D. F. Bogdanski, et al., J. Pharmacol. Exp. Ther., 122, 182 (1958) which measures the effect of the test compound on the 5-hydroxytryptophan(5-HTP)-induced syndrome. In this test the degree of intensity of the 5-HTP-induced syndrome, i.e. extension and abduction of hind-limbs, lordosis, tremors, head movements and excitation, following the administration of the test compound to Swiss albino mice, is indicated by a scale ranging from +1 (weak effect) to +4 (very strong effect). A positive score in the test is indicative of antidepressant agents having desirable mood elevation properties, see A. Carlsson, et al., Eur. J. Pharmacol., 5, 357 (1969). Several of the preferred compounds, for example, 2-(ethylamino)-4-(1-naphthyloxy)-1-butanol hydrochloride, produces a significant effect (+1 to +3) on the 5-HTP-induced syndrome at doses of 6.25 to 25 mg/kg, i.p., when administered to mice (five per group) 30 minutes prior to the 5-HTP injection (300 mg/kg, i.p.).

The following table illustrates further a comparative study of 2-(ethylamino)-4-(1-naphthyloxy)-1-butanol hydrochloride, imipramine hydrochloride and desimipramine hydrochloride in the potentiation of the 5-HTP-syndrome test.

| Compound | Dose(mg/kg,i.p.) | Behavioral Score |
|---|---|---|
| saline | — | 0 |
| 2-(ethylamino)-4-(1-naphthyloxy)-1-butanol hydrochloride(Example 6) | 25 | +3 |
|  | 12.5 | +3 |
|  | 6.25 | +1 |
| imipramine hydrochloride | 25 | +3 |
|  | 12.5 | +2 |
|  | 6.25 | +1 |
| desimipramine hydrochloride | 25 | +1 |

When the compounds of formula 1 are used as antidepressants in mammals, e.g. rats and mice, they may be used alone or in combination with pharmacologically acceptable carriers, the proportion of which is determined by the solubility and chemical nature of the compound, chosen route of administration and standard biological practice. For example, they are administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in a range of from about 0.1 mg to about 100 mg/kg per day, although as aforementioned variations will occur. However, a dosage level that is in the range of from about 0.5 mg to about 50 mg/kg per day is most desirably employed in order to achieve effective results.

The compounds of formula 1 in which $R^1$ is hydrogen and Ar, $R^2$ and $R^3$ are as defined herein and $R^4$ is hydrogen or lower alkyl containing from one to five carbon atoms are prepared by a process represented by the following flow diagram.

Ar—OCH$_2$CH$_2$CHCOOH →
  |
2  NH$_2$ 1 ($R^1$, $R^2$ and $R^3$ = H) →

-continued

Ar—OCH$_2$CH$_2$CHCH$_2$OCOR$^4$
  |
3  NHCOR$^4$  →

1 ($R^1$ and $R^3$ = H, $R^2$ = lower alkyl) →

Ar—OCH$_2$CH$_2$CHCH$_2$OCOR$^4$
  |
4  NR$^2$COR$^4$  →

1 ($R^1$ = H, $R^2$ and $R^3$ = lower alkyl)

The starting material of formula 2 in which Ar is phenyl, 2-amino-4-phenoxybutanoic acid, has been described by Y. Knobler, et al., J. Org. Chem., 24, 1974 (1959) and the starting material of formula 2 in which Ar is 1-naphthyl, 2-amino-4-(1-naphthyloxy)-butanoic acid, can be prepared from 1-naphthol by following the procedure described in the Y. Knobler, et al. publication, see Example 1.

With reference to the flow diagram, it will be seen that the compounds of formula 1 in which $R^1$ is hydrogen are obtained from a series of reduction and acylation steps.

More specifically, reduction of the starting material of formula 2 with diborane or an amine-diborane complex gives the corresponding compound of formula 1 in which $R^1$, $R^2$ and $R^3$ are hydrogen (i.e. a primary amine of formula 1 in which $R^1$ is hydrogen). If a compound of formula 1 in which $R^1$ and $R^3$ are hydrogen and $R^2$ is lower alkyl is desired, subsequent acylation of the latter primary amine affords the acyloxyamide of formula 3 in which $R^4$ is hydrogen or a lower alkyl containing from one to five carbon atoms, which upon reduction with a complex metal hydride affords the corresponding compound of formula 1 in which $R^1$ and $R^3$ are hydrogen and $R^2$ is lower alkyl (i.e., a secondary amine of formula 1 in which $R^1$ is hydrogen). Thereafter, if an amine compound of formula 1 in which $R^1$ is hydrogen and $R^2$ and $R^3$ are lower alkyl is desired, then the above noted secondary amine compound is acylated to give the corresponding acyloxyamide of formula 4 which in turn is reduced with a complex metal hydride to give the compound of formula 1 in which $R^1$ is hydrogen and $R^2$ and $R^3$ are lower alkyl (i.e. a tertiary amine of formula 1 in which $R^1$ is hydrogen).

Still more specifically, the reduction of the starting material of formula 2 with diborane or an amine-diborane complex, for example diborane complexes with ethylamine or tert-butyl amine, is conveniently performed by bringing the starting material into contact with two to five molar equivalents of the reducing agent in an inert organic solvent, for example, tetrahydrofuran or ether, at temperatures of −10 to 80° C., or the boiling points of the reaction mixture. A reaction period of 30 minutes to two or three days is employed. The reaction is usually initiated at 0 to 10° C. and then allowed to come to room temperature. In this manner the primary amine compound of formula 1 in which $R^1$, $R^2$ and $R^3$ each are hydrogen is obtained.

With reference to the subsequent acylation reaction, i.e. transformation of a compound of formula 1 in which $R^1$, $R^2$ and $R^3$ each are hydrogen to the corresponding compound of formula 3, two approaches are possible depending on whether $R^4$ of the compound of formula 3 is hydrogen or lower alkyl. When it is desired to obtain the compound of formula 3 in which $R^4$ is hydrogen, the latter primary amine compound of formula 1 is acylated with formic acid, preferably in the presence of acetic anhydride, at 10 to 80° C. for two to 24 hours, preferably at 20 to 30° C. for 16 to 20 hours.

When it is desired to obtain the compound of formula 3 in which $R^4$ is a lower alkyl containing from one to five carbon atoms, the latter primary amine compound of formula 1 is acylated with the appropriate lower alkanoic anhydride or lower alkanoic acid halide in the presence of a proton acceptor, for example, pyridine or triethylamine. Usual conditions for this acylation include a reaction time of four to 24 hours at 20 to 50° C., preferably 20 to 25° C.

Next, the compound of formula 3 is reduced with a suitable complex metal hydride to yield the corresponding secondary amine of formula 1 in which $R^1$ and $R^2$ are hydrogen and $R^3$ is lower alkyl. Examples of suitable complex metal hydrides are lithium aluminum hydride, lithium aluminum chloride, aluminum hydride - aluminum chloride, diborane and sodium borohydride - aluminum chloride. Lithium aluminum hydride is preferred.

Thereafter, when it is desired to obtain the tertiary amine compound of formula 1 in which $R^1$ is hydrogen and $R^2$ and $R^3$ are lower alkyl, the above secondary amine compound is subjected to the acylation condition described above to obtain the corresponding compound of formula 4 which in turn is reduced with a suitable complex metal hydride in the same manner as described above.

The compounds of formula 1 in which $R^1$ is lower alkyl and Ar, $R^2$ and $R^3$ are as defined herein and $R^4$ is hydrogen or lower alkyl containing one to five carbon atoms are prepared by a process represented by the following flow diagram.

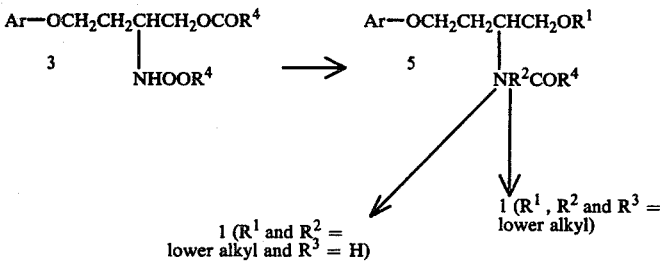

With reference to the preceding flow diagram, the starting materials of formula 3 are described hereinabove.

In the practice of the process, the starting material of formula 3 is subjected to alkylation with an appropriate lower alkyl halide to give the corresponding compound of formula 5. Convenient conditions for effecting this alkylation include the use of a proton acceptor, for example sodium hydride or sodium carbonate, and an inert organic solvent, for example, tetrahydrofuran benzene or acetone; sodium hydride and tetrahydrofuran being preferred, respectively, for the proton acceptor and inert organic solvent. The time needed to complete this reaction usually varies from about two to 24 hours at temperatures ranging from 20 to 100° C. or the boiling point of the reaction mixture. In this manner the compound of formula 5 in which Ar is as defined herein and $R^1$ and $R^2$ are the same lower alkyl is obtained.

Thereafter, the compound of formula 5 is reduced with a suitable complex metal hydride in the manner described above to give the corresponding compound of formula 1 in which $R^1$, $R^2$ and $R^3$ are each lower alkyl. Alternatively, said compound of formula 5 is subjected to basic hydrolysis to give the corresponding compound of formula 1 in which $R^1$ and $R^2$ are lower alkyl and $R^3$ is hydrogen. For the basic hydrolysis a preferred embodiment involves subjecting the compound of formula 5 to the action of a strong base, for example, sodium or potassium hydroxide, in the presence of sufficient water to effect hydrolysis. The hydrolysis is performed using a suitable solvent, for example methanol or ethanol, and the reaction mixture is maintained at a temperature of from 25° C. to the reflux temperature of the mixture until hydrolysis occurs. Usually from ten minutes to six hours is sufficient for this hydrolysis. The reaction mixture is extracted with an organic solvent, for example diethyl ether, and the extract worked up in the usual manner to afford the compound of formula 1 in which $R^1$ and $R^2$ are the same lower alkyl and $R^3$ is hydrogen.

The following examples illustrate further this invention.

EXAMPLE 1

2-Amino-4-(1-naphthyloxy)butanoic Acid (2; Ar = 1-naphthyl)

By following the procedure of Y. Knobler, et al., J. Org. Chem., 24, 1794 (1959), the title compound is prepared. An example follows:

To a solution of 1-naphthol (7.2 g) in diglyme (70 ml), sodium (1.269) is added portionwise. The mixture is heated at reflux for 4 hours and cooled to between 30 and 40° C. α-Phthalimido-γ-butyrolactone [10.49g, described by G. Talbot, et al., Can. J. Chem., 36, 593 (1958)] is added to the mixture keeping the temperature between 30 and 40° C. Thereafter, the mixture is heated at reflux for 4 hours. Cooling the mixture and adding ether precipitates the sodium salt of 2,2-dihydro-α-[2-(1-naphthyloxy)ethyl]-1,3-dioxo-1H-isoindole-2-acetic acid as a solid. The solid is collected, washed carefully with ether and dissolved in a minimum amount of water. The solution is adjusted to pH 6 by the addition of dilute hydrochloric acid and extracted with diethyl ether. The extract is dried and evaporated to give 2,2-dihydro-α-[2-(1-naphthyloxy)ethyl]-1,3-dioxo-1H-isoindole-2-acetic acid, mp 136–138° C. after crystallization from benzene-petroleum ether (40–60° C.).

A solution of the latter compound (30 g) and hydrazine hydrate (10 ml) in ethanol (510 ml) is heated at reflux for 2 hours. The resulting solid is collected by filtration. The filtrate is evaporated. The residue is dissolved in 2N HCl(390 ml) and heated at reflux for 2 hours. The mixture is cooled and the solid collected by filtration and washed with hot water. The combined filtrate and washings are rendered neutral with conc. ammonium hydroxide. The resulting solid is collected, washed with water and dried to give the title compound, mp 238–239° C., after crystallization from methanol.

EXAMPLE 2

2-Amino-4-(1-naphthyloxy)-1-butanol (1; Ar= 1-naphthyl, $R^1$, $R^2$ and $R^3$ = H In a nitrogen atmosphere at 0°0 C. a one molar solution of diborane in THF (100 ml) is added to a solution of 2-amino-4-(1-naphthyloxy)butanoic acid (24.0 g), prepared as described in Example 1, in 70 ml of tetrahydrofuran (THF). Two additional 100 ml portions are added to the reaction mixture, one after 2 hours and one after 3 hours. The reaction mixture is then left at 20–25° C. for 16 hours. Excess diborane is carefully destroyed with 10% HCl. Water is added and the THF evaporated under reduced pressure. The aqueous phase is extracted twice with diethyl ether (250 ml). The aqueous phase is then adjusted to pH 8–8.5 and extracted twice with chloroform ($CHCl_3$) and twice with diethyl ether. Both extracts are washed, dried and evaporated to dryness. The combined oily residues are crystallized from diethyl ether to give the title compound, $\gamma_{max}^{CHCl_3}$ 3360, 1580 and 1592 cm$^{-1}$.

The corresponding hydrochloric acid addition salt (hydrochloride) has mp 172° C., after recrystallization from methanol-diethyl ether.

In the same manner but replacing 2-amino-4-(1-naphthyloxy)butanoic acid with an equivalent amount of 2-amino-4-phenoxy-butanoic acid, described by Y. Knobler, et al., J. Org. Chem., 24, 1794 (1959), 2-amino-4-phenoxy-1-butanol, $\gamma_{max}^{CHCl_3}$ 3230–3400, is obtained. The hydrochloric acid addition salt of 2-amino-4-phenoxy-1-butanol has mp 136–138° C., after recrystallization from methanol-diethyl ether.

EXAMPLE 3

2-(Formylamino)-4-(1-naphthyloxy)-1-butanol Formate (3; Ar = 1-naphthyl and $R^4$ = H A mixture of formic acid (22 ml) and acetic acid (22 ml) is heated at 50° C. for 2 hours and then cooled to between 20 and 25° C. 2-Amino-4-(1-naphthyloxy)-1-butanol (8.5 g), prepared as described in Example 2, is added and the mixture stirred for 16 hours. The mixture is poured into a mixture of ice and water and extracted with $CHCl_3$. The organic extract is washed with dilute sodium bicarbonate, water, dried and evaporated. The oily residue is crystallized from diethyl ether to give the title compound, mp 112° C.

In the same manner but replacing 2-amino-4-(1-naphthyloxy)-1-butanol with an equivalent amount of 2-amino-4-phenoxy-1-butanol, described in Example 2, 2-(formylamino)-4-phenoxy-1-butanol formate is obtained.

EXAMPLE 4

2-(Methylamino)-4-(1-naphthyloxy)-1-butanol (1; Ar = 1-naphthyl, $R^1$ and $R^3$ = H, and $R^2$ = $CH_3$)

A solution of 2-(formylamino)-4-(1-naphthyloxy)-butanol (7.1 g), prepared as described in Example 3, in dry THF (150 ml) is added dropwise to a suspension of $LiAlH_4$ (5.0 g) in THF (150 ml). The mixture is heated at 45° C. for 3 hours and cooled. Excess $LiAlH_4$ is destroyed by the careful addition of THF/water (9:1). The mixture is filtered through diatomaceous earth (Celite). The filtrate is dried and evaporated. The residue is crystallized from diethyl ether to give the title compound, $\gamma_{max}^{CHCl_3}$ 3650, 3352, 1595 and 1580 cm$^{-1}$.

The maleic acid addition salt (maleate) of the title compound has mp 101–102° C., after recrystallization from methanol-diethyl ether.

In the same manner but replacing 2-(formylamino)-4-(1-naphthyloxy)butanol with an equivalent amount of 2-(formylamino)-4-phenoxy-1-butanol, described in Example 3, 2-(methylamino)-4-phenoxy-1-butanol, $\gamma_{max}^{CHCl_3}$ 3220–3400 cm$^{-1}$, is obtained. The corresponding maleic acid addition salt of the latter compound has mp 105–106° C.

EXAMPLE 5

2-(Acetylamino)-4-(1-naphthyloxy)-1-butanol Acetate

2-Amino-4-(1-naphthyloxy)-1-butanol, described in Example 2, is acetylated with acetic anhydride in the presence of pyridine in the usual manner to give the title compound, $\gamma_{max}^{CHCl_3}$ 3440, 1730 and 1660 cm$^{-1}$.

In the same manner but replacing acetic anhydride with propionic anhydride or butanoic anhydride, 2-(propionylamino)-4-(1-naphthyloxy)-butanol propionate and 2-(butanoylamino)-4-(1-naphthyloxy)butanol butyrate are obtained, respectively.

In the same manner but replacing 2-amino-4-(1-naphthyloxy)-1-butanol with 2-amino-4-phenoxy-1-butanol, described in Example 2, 2-(acetylamino)-4-phenoxybutanol acetate is obtained.

In the same manner but replacing 2-amino-4-(1-naphthyloxy)-1-butanol with 2-amino-4-phenoxy-1-butanol, described in Example 2, and replacing acetic anhydride with propionic anhydride or butanoic anhydride, 2-(propionylamino)-4-phenoxy-butanol propionate and 2-(butanoylamino)-4-phenoxy-butanol butyrate are obtained, respectively.

EXAMPLE 6

2-(Ethylamino)-4-(1-naphthyloxy)-1-butanol (1; Ar = 1-naphthyl, $R^1$ and $R^3$ = H and $R^2$ = $C_2H_5$)

A solution of 2-(acetylamino)-4-(1-naphthyloxy)-butanol acetate (5.1 g), described in Example 5, in diethyl ether (40 ml) and dry THF (8 ml) is added to a suspension of $LiAlH_4$ in diethyl ether (30 ml). The mixture is heated at reflux in nitrogen atmosphere for 24 hours. Excess $LiAlH_4$ is destroyed with ethyl acetate and water. The reaction mixture is worked up in the manner described in Example 4. The product is crystallized from ether-hexane to give the title compound, mp 78–81° C., nmr ($CDCl_3$) δ1.1 (t, J = 7Hz, 5H), 2.1 (m, 2H), 2.4 (2H), 2.75 (q, J = 7Hz, 5H), 4.25 (t, J = 6.5 Hz, 2H), 6.8 and 8.4 (7H).

The corresponding hydrochloric acid addition salt of the title compound has mp 105–107° C., after recrystallization from acetone-benzene-hexane.

In the same manner but replacing 2-(acetylamino)-4-(1-naphthyloxy)butanol acetate with an equivalent amount of
2-(propionylamino)-4-(1-naphthyloxy)butanol propionate,
2-(butanoylamino)-4-(1-naphthyloxy)butanol butyrate,
2-(acetylamino)-4-phenoxy-1-butanol acetate, $\gamma_{max}^{CHCl_3}$ 1735 and 1660 cm$^{-1}$,
2-(propionylamino)-4-phenoxy-1-butanol propionate, or
2-(butanoylamino)-4-phenoxy-1-butanol butyrate,
the following compounds of formula 1,
2-(propylamino)-4-(1-naphthyloxy)-1-butanol,
2(butylamino)-4-(1-naphthyloxy)-1-butanol, 2-(ethylamino)-4-phenoxy-1-butanol, nmr (DMSO-D$_6$) δ 3.8 (2H), 4.15 (2H),
2-(propylamino)-4-phenoxy-1-butanol, and
2-(butylamino)-4-phenoxy-1-butanol, are obtained respectively.

The corresponding hydrochloric acid addition salt of 2-(ethylamino)-4-phenoxy-butanol has mp 114–115° C., after recrystallization from acetone-diethyl ether.

EXAMPLE 7

2-(Dimethylamino)-4-(1-naphthyloxy)-1-butanol (1; Ar = 1-naphthyl, R$^1$ = H, and R$^2$ and R$^3$ = CH$_3$ 2-(Formylmethylamino)-4-(1-naphthyloxy)-1-butanol formate is prepared from 2-(methylamino)-4-(1-naphthyloxy)-1-butanol described in Example 4, by treatment with formic acid in acetic anhydride in the manner described in Example 3. Thereafter the oily 2-(formylmethylamino)-4-(1-naphthyloxy)-1-butanol formate, $\gamma_{max}^{CHCl_3}$ 1720 and 1665 cm$^{-1}$, is reduced with LiAlH$_4$ in the manner described in Example 4 to give the title compound, nmr (CDCl$_3$) δ 1.8 (m, 2H), 2.35 (s, 6H), 2.75 (broad, 1H), 3.6 (m, 3H), 4.18 (t, J = 7Hz, 2H) and 6.7–8.3 (7H).

The corresponding maleic acid addition salt of the title compound has mp 102–103° C., after recrystallization from methanol-diethyl ether.

In the same manner but replacing 2-(methylamino)-4-(1-naphthyloxy)-1-butanol with an equivalent amount of the appropriate compound of formula 1 in which Ar is as defined herein, R$^1$ and R$^3$ are hydrogen and R$^2$ is lower alkyl, i.e. compounds described in Examples 4 and 6, and using the appropriate acylating agent, corresponding compounds of formula 1 in which R is hydrogen and R$^2$ and R$^3$ each are lower alkyl are obtained.

For example,
2-(methylamino)-4-phenoxy-1-butanol, described in Example 4, with formic acid, followed by reduction, gives 2-(dimethylamino)-4-phenoxy-1-butanol, 2-(propylamino)-4-phenoxy-1-butanol, described in Example 6, with propionic anhydride, followed by reduction, gives 2-(dipropylamino)-4-phenoxy-1-butanol, 2-(ethylamino)-4-(1-naphthyloxy)-1-butanol, described in Example 6, with formic acid, followed by reduction, gives 2-(ethylmethylamino)-4-(1-naphthyloxy)-1-butanol, and 2-(butylamino)-4-(1-naphthyloxy)-1-butanol, described in Example 6, with acetic anhydride, followed by reduction, gives 2-(butylethylamino)-4-(1-naphthyloxyl)-1-butanol.

EXAMPLE 8

N-[1-(Methoxymethyl)-3-(1-naphthyloxy)propyl]-N-methylformamide (5; Ar = 1-naphthyl, R$^2$ = CH$_3$ and R$^4$ = H)

A solution of 2-(formylamino)-4-(1-naphthyloxy)-1-butanol formate, described in Example 3, in THF (30 ml) is added dropwise to a suspension of 51% sodium hydride (600 mg) in THF (30 ml). The mixture is heated at 40° C. for one and a half hours and then cooled to room temperature. A solution of methyl iodide (2.4 g) in THF (10 ml) is added and the mixture stirred at room temperature for 18 hours. Excess sodium hydride is decomposed by the addition of THF/water (9:1). The mixture is filtered through diatomaceous earth (Celite). The filtrate is dried and evaporated to dryness. The oily residue is subjected to chromatography on silica gel. Elution with methanol-chloroform (1:30) gives the title compound, nmr(CDCl$_3$) δ 2.05 (m, 2H), 2.85 (s, 3H), 3.35 (s, 3H), 3.6 L (m, 1H), 4.15 (m, 4H), 6.75–8.35 (7H), 8.15 (s, 1H).

EXAMPLE 9

1-Methoxy-N,N-dimethyl-4-(1-naphthyloxy)-2-butanamine (1; Ar = 1-naphthyl, and R$^1$, R$^2$ and R$^3$ = CH$_3$).

N-[1-(Methoxymethyl)-3(1-naphthyloxy)propyl]-N-methylformamide, described in Example 8, is reduced with LiAlH$_4$ in the manner described in Example 4 to give the title compound, nmr (CDCl$_3$) δ 2.05 (m, 2H), 2.35 (s, 6H), 3.0 (s, 1H), 3.35 (s, 3H), 3.5 (m, 2H), 4.25 (t, J = 5.5Hz, 2H) and 6.75–8.4 (7H).

The corresponding hydrochloric acid addition salt (hydrochloride) of the title compound has mp 140–141° C., after recrystallization from acetone-diethyl ether.

By following serially Examples 8 and b 9 but replacing 2-(formylamino)-4-(1-naphthyloxy)-1-butanol formate with an equivalent amount of the appropriate compound of formula 3 in which Ar is as defined herein, i.e. compounds described in Examples 3 and 5, and using the appropriate lower alkyl halide, other compounds of formula 1 in which R$^1$, R$^2$ and R$^3$ are lower alkyl are obtained.

For example,
2-(formylamino)-4-phenoxy-1-butanol formate, described in Example 3, with methyl iodide, followed by reduction, gives 1-methoxy-N,N-dimethyl-4-phenoxy-2-butanamine, 2-(propionylamino)-4-phenoxy-1-butanol propionate, described in Example 5, with propyl iodide, followed by reduction gives 1-propoxy-N,N-dipropyl-4-phenoxy-2-butanamine, 2-(acetylamino)-4-(1-naphthyloxy)-1-butanol acetate, described in Example 5, with methyl iodide, followed by reduction, gives 1-methoxy-N-ethyl-N-methyl-4-(1-naphthyloxy)-2-butanamine, and 2-(butanoylamino)-4-(1-naphthyloxy)butanol butyrate, described in Example 5, with ethyl chloride, followed by reduction, gives 1-ethoxy-N-butyl-N-ethyl-4-(1-naphthyloxy)-2-butanamine.

We claim:

1. A compound of formula 3

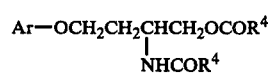

in which Ar is phenyl or 1-naphthyl and R$^4$ is hydrogen or lower alkyl containing from one to five carbon atoms.

2. 2-(Formylamino)-4-(1-naphthyloxy)-1-butanol formate, as claimed in claim 1.

3. 2-(Acetylamino)-4-(1-naphthyloxy)-1-butanol acetate, as claimed in claim 1.

4. 2-(Acetylamino)-4-phenoxy-1-butanol acetate, as claimed in claim 1.

5. A compound of formula 4

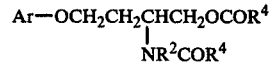

in which Ar is phenyl or 1-naphthyl, R$^2$ is lower alkyl and R$^4$ is hydrogen or lower alkyl containing from one to five carbon atoms.

6. 2-(Formylmethylamino)-4-(1-naphthyloxy)-1-butanol formate as claimed in claim 5.

7. A compound of formula 5

$$Ar\text{—}OCH_2CH_2CHCH_2OR^1$$
$$\phantom{Ar\text{—}OCH_2CH_2C}|$$
$$\phantom{Ar\text{—}OCH_2CH_2}NR^2COR^4$$

in which Ar is phenyl or 1-naphthyl, $R^1$ and $R^2$ are the same lower alkyl and $R^4$ is hydrogen or lower alkyl containing from one to five carbon atoms.

8. N-[1-(Methoxymethyl)-3-(1-naphthyloxy)propyl]-N-methylformamide, as claimed in claim 7.

* * * * *